US006919087B2

(12) United States Patent
Lemmens et al.

(10) Patent No.: US 6,919,087 B2
(45) Date of Patent: Jul. 19, 2005

(54) PHARMACEUTICAL COMPOSITIONS COMPRISING AMLODIPINE MALEATE

(75) Inventors: Jacobus M. Lemmens, Mook (NL); Frans van Dalen, Nijmegen (NL); Arlette Vanderheijden, Nijmegen (NL)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 09/938,816

(22) Filed: Aug. 27, 2001

(65) Prior Publication Data

US 2002/0176889 A1 Nov. 28, 2002

Related U.S. Application Data

(63) Continuation-in-part of application No. 09/809,346, filed on Mar. 16, 2001, now abandoned.
(60) Provisional application No. 60/258,562, filed on Dec. 29, 2000.

(51) Int. Cl.$^7$ .................................................. A61K 9/00
(52) U.S. Cl. ..................... 424/400; 451/452; 451/464; 451/465; 451/489; 514/350; 514/355; 514/356; 546/321
(58) Field of Search ................................ 424/400, 451, 424/452, 463, 464, 465, 474, 489, 457, 458, 459, 470; 546/321; 514/350, 355, 356

(56) References Cited

U.S. PATENT DOCUMENTS

| 4,572,909 | A | | 2/1986 | Campbell et al. | |
|---|---|---|---|---|---|
| 4,590,195 | A | | 5/1986 | Alker et al. | |
| 4,687,662 | A | * | 8/1987 | Schobel | ........................ 424/44 |
| 4,879,303 | A | | 11/1989 | Davison et al. | |
| 4,983,740 | A | | 1/1991 | Peglion et al. | |
| 5,155,120 | A | | 10/1992 | Lazar et al. | |
| 5,389,654 | A | | 2/1995 | Furlan et al. | |
| 5,438,145 | A | | 8/1995 | Furlan et al. | |
| 5,585,115 | A | * | 12/1996 | Sherwood et al. | .......... 424/489 |
| 6,046,337 | A | | 4/2000 | Bozsing et al. | |
| 6,057,344 | A | | 5/2000 | Young | |
| 6,471,946 | B1 | * | 10/2002 | Takatsuka et al. | ............ 424/52 |

FOREIGN PATENT DOCUMENTS

| EP | 0 089 167 B1 | | 10/1986 |
|---|---|---|---|
| EP | 0 244 944 | | 1/1990 |
| EP | 0 290 211 B1 | | 9/1991 |
| EP | 0 534 520 B1 | | 3/1997 |
| EP | 0 902 016 A1 | | 3/1999 |
| EP | 0 963 980 A2 | | 12/1999 |
| WO | WO 95/34299 | | 12/1995 |
| WO | WO 98/26765 | * | 6/1998 |
| WO | 99/25688 | | 5/1999 |
| WO | 99/52873 | | 10/1999 |
| WO | 00/24714 | | 5/2000 |
| WO | 00/35873 | | 6/2000 |
| WO | 00/35910 | | 6/2000 |

OTHER PUBLICATIONS

Colowick and Kaplan. Methods in Enzymology Volume !, Academic Press Inc. 1995, p. 143.*
Nahata et al., "Stability of enalapril maleate in three . . . ", Am J Health–Syst Pharm vol. 55, Jun. 1998, pp 1155–1157.
Rompp Chemie Lexikon, 9th Ed. 1991, p 2771.
Nahata et al., J Am Pharm Assoc., vol. 39, No. 3, May/Jun. 1999, pp 375–377.
Alker et al., "Long–acting dihydropyridine calcium antagonists. 9. Structure activity relationships around amlodipine", Eur J Med Chem (1991) 26, 907–913.
Amlodipine Besylate Monograph, Pharmeuropa vol. 10, No. 2, 197–198, Jun. 1998.
Faulkner et al, "Absorption of Amlodipine Unaffected by Food", Arzneim Forsch/Drug Res. 39(11), No. 7, (1989).
McDaid and Deasy, "Formulation development of a transdermal drug delivery system for amlodipine base", International Journal of Pharmaceutics 133 (1996) 71–83.
Arrowsmith et al., "Long–Acting Dihydropyridine Calcium Antagonists. 1. 2–Alkoxymethyl Derivatives Incorporating Basic Substituents", J. Med. Chem. American Chemical Society, 1986, 29, 1696–1702.
FDA FOIA Material on Amlodipine Besylate, NDA No. 19–787, "Review of an Original NDA", Oct. 10, 1990.

* cited by examiner

*Primary Examiner*—Gary L. King
*Assistant Examiner*—Sharmila S. Gollamudi
(74) *Attorney, Agent, or Firm*—Mark R. Buscher

(57) ABSTRACT

An amlodipine maleate pharmaceutical composition is provided with good stability when formulated with a pH within the range of 5.5 to 7, when measured as a 20 wt % aqueous slurry. The stability can also be aided by making the pharmaceutical composition from amlodipine maleate particles having an average particle size of greater than 20 microns, preferably greater than 100 microns.

38 Claims, No Drawings

PHARMACEUTICAL COMPOSITIONS COMPRISING AMLODIPINE MALEATE

This application is a Continuation In Part application under 35 U.S.C. § 120 of prior U.S. patent application Ser. No. 09/809,346, filed Mar. 16, 2001, now abandoned, the entire contents of which are incorporated herein by reference. Further, this application claims the benefit of priority under 35 U.S.C. § 119(e) from U.S. provisional application No. 60/258,562, filed Dec. 29, 2000, the entire contents of which are incorporated herein by reference.

BACKGROUND OF THE INVENTION

1. Field of the Invention

The present invention relates to pharmaceutical compositions comprising amlodipine maleate and to processes for making the same.

2. Description of the Related Arts

Calcium channel blockers are useful in treating a variety of cardiac conditions, primarily angina and hypertension. EP 089 167 and corresponding U.S. Pat. No. 4,572,909 disclose a class of substituted dihydropyridine derivatives as being useful calcium channel blockers. These patents identify that one of the most preferred compounds is 2-[(2-aminoethoxy) methyl]-4-(2-chlorophenyl)-3-ethoxycarbonyl-5-methoxycarbonyl-6-methyl-1,4-dihydropyridine. This compound, which is now commonly known as amlodipine, has the following formula:

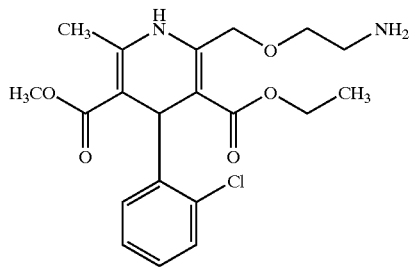

Examples 8, 11, 12, and 22 of EP 089 167 show the synthesis of amlodipine in the maleate salt form. While a variety of acid addition salts are taught to be suitable, the maleate salt is identified as the most preferred acid addition salt.

Subsequently, EP 244 944 and corresponding U.S. Pat. No. 4,879,303 were issued directed to the besylate (or benzene sulfonate) salt of amlodipine. The besylate salt is stated to provide certain advantages over the known salts including good formulating properties. Indeed, amlodipine besylate, and not amlodipine maleate, has been developed into a commercial prescription pharmaceutical by Pfizer and is sold in the U.S. under the trade name NORVASC.

A review of the available portions of the NORVASC (amlodipine besylate) New Drug Application (NDA) filed with the U.S. Food & Drug Administration by Pfizer reveals that a switch was made during development from the original amlodipine maleate to the amlodipine besylate. (See "Review of Original NDA" for NDA# 19-787 of Oct. 10, 1990, obtainable from FDA under Freedom of Information Act). The reasons for the switch were apparently tabletting and stability problems. However, the precise stability and tabletting problems/issues/causes are not publicly disclosed in the information available from the FDA. Interestingly, clinical studies in the NDA include the use of the maleate salt form and the besylate salt form, the two salt forms being therapeutically equivalent (bioequivalent). However, in these studies amlodipine maleate was always used in a capsule or solution dosage form, not a tablet dosage form.

SUMMARY OF THE INVENTION

The present invention relates to the discovery of stable amlodipine maleate pharmaceutical compositions. A first aspect of the invention relates to a pharmaceutical composition comprising an effective amount of amlodipine maleate and at least one pharmaceutically acceptable excipient wherein the composition has a pH within the range of 5.5–7.0. The composition is preferably a solid dosage form such as a tablet or capsule. The invention also relates to methods of making such a composition as well as to the use of such compositions in treating or preventing angina or hypertension.

Another aspect of the invention relates to a process which comprises mixing solid particles of amlodipine maleate having an average particle size of at least 20 microns with one or more pharmaceutically acceptable excipients to form a mixture. Preferably the mixture has a pH of from 5.5 to 7.0. The mixture can be compressed into tablets or filled into capsules to form a solid dosage form.

DETAILED DESCRIPTION OF THE INVENTION

Stability is an important aspect of a pharmaceutical composition. The present invention is based on the discovery that the prior art stability problems associated with amlodipine maleate can be overcome primarily by controlling the pH of the composition to be within the range of about 5.5 to 7.0, preferably of about 6.0–7.0. Within this range the potential degradation reactions are minimized. In particular, the formation of the following degradation product, referred to herein as amlodipine aspartate, is diminished or prevented in this pH range.

Amlodipine Aspartate

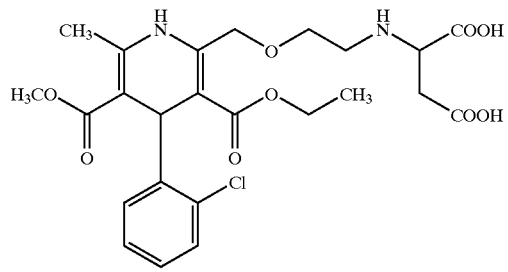

Amlodipine aspartate is formed by a Michael addition reaction between amlodipine and maleic acid. Because amlodipine and maleic acid are in intimate contact with each other in the amlodipine maleate salt, the chances of the addition reaction occurring increase with time; hence raising a stability issue. By controlling the pH, the addition is significantly slowed or prevented altogether. Thus, it has now been discovered that pH levels above 7.0 tend to encourage the degradation of amlodipine maleate into amlodipine aspartate. Below a pH of about 5.5, other degradation reactions tend to be encouraged, including the pyridine analogue of amlodipine having the following structure:

"Amlo-Pyridine"

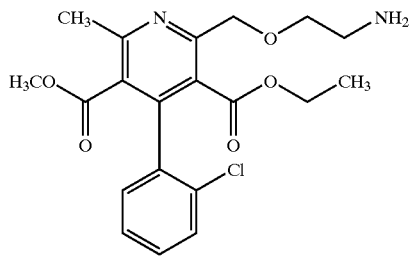

Preferably the pH of the stabilized composition of our invention is in the range of about 6.0 to 7.0 and more typically from about 6.1 or 6.2 to 6.8. For solid compositions, the pH is determined by forming a slurry of the material with water (demineralized water) and measuring the pH of the slurry, as is understood by workers skilled in the art regarding the pH of a solid composition. The concentration of the composition in the slurry is 20 wt %. The pH is measured by any standard technique.

The pharmaceutical compositions of the present invention comprise a pharmaceutically effective amount of amlodipine maleate and at least one pharmaceutically acceptable excipient. Preferably the stability of the composition is such that after three months, more preferably after six months, in an environment controlled room at 40° C./75% RH, it exhibits a loss of amlodipine (or, accordingly, an increase in impurities content) of less than 10%, preferably less than 5%, and more preferably less than 1%. Alternatively, the amlodipine maleate pharmaceutical compositions of the present invention preferably exhibit a storage stability equivalent to or superior to amlodipine besylate compositions. For example, the loss of amlodipine during storage to degradation reactions is equivalent to (+/−10%) or less than the amlodipine loss in amlodipine besylate compositions, especially the commercial product.

The form of the amlodipine maleate is not particularly limited and includes anhydrates, solvates, hydrates and partial hydrates as well as crystalline and amorphous forms. Further, the ratio of amlodipine to maleate can be varied and specifically includes the more common and prior art form of 1:1 as well as a novel 2:1 form described commonly owned co-pending U.S. patent application Ser. No. 09/809,356, filed on Mar. 16, 2001, and entitled "Amlodipine Hemimaleate," the entire contents of which are incorporated herein by reference.

The amount of amlodipine is not particularly limited and includes any amount that provides a pharmaceutical effect. In particular, amlodipine maleate can be used to treat or prevent hypertension or angina by administering an effective amount to a patient in need thereof. The specific form of angina is not particularly limited and specifically includes chronic stable angina pectoris and vasospastic angina (Prinzmetal's angina). The compound can be administered by any suitable route including orally or parenterally depending on the dosage form. The "patients" intended to be treated include human and non-human animals especially non-human mammals. Generally the amount of amlodipine maleate in a unit dose is from 1 to 100 mg, more typically from 1 to 25 mg, and preferably about 1, 1.25, 2.5, 5 or 10 mg (expressed in terms of the free base).

Amlodipine maleate can be made by any of the known techniques set forth in the prior art, including those described in the above-mentioned patents EP 089 167 and U.S. Pat. No. 4,572,909. It is desirable that the amlodipine maleate active be substantially pure. For example, the content of impurities such as amlodipine aspartate, amlopyridine, etc. that can be produced during the synthesis should be limited, preferably to less than 2 wt %, although such purity is not required for the present invention. A useful method to produce amlodipine maleate substantially free from amlodipine aspartate is described in commonly owned co-pending U.S. patent application Ser. No. 09/809,343, filed on Mar. 16, 2001, and entitled "Process for Making Amlodipine Maleate," the entire contents of which are incorporated by reference. Similarly, a useful method for making amlodipine free base is described in commonly owned co-pending U.S. patent application Ser. No. 09/809,351, filed on Mar. 16, 2001, and entitled "Process For Making Amlodipine, Derivatives Thereof, and Precursors Therefor," the entire contents of which are incorporated herein by reference.

The pharmaceutical compositions of the present invention also contain at least one excipient. An "excipient" as used herein means any pharmaceutically acceptable inactive component of the composition. As is well known in the art, excipients include diluents, binders, lubricants, disintegrants, colorants, preservatives, pH-adjusters etc. The excipients are selected based on the desired physical aspects of the final form: e.g., obtaining a tablet with desired hardness and friability, being rapidly dispersible and easily swallowed, etc. The desired release rate of the active substance from the composition after its ingestion also plays a role in the choice of excipients. Preferred release rate is the rate comparable with commercially available amlodipine besylate tablets.

Suitable excipients for use in this invention include:

a diluent such as calcium hydrogen phosphate, lactose, mannitol etc.

a binder such as microcrystalline cellulose or a modified cellulose, povidone etc.

a disintegrant such as sodium starch glycollate, crosspovidone a lubricant such as magnesium stearate, sodium stearyl fumarate, talc a colorant, taste masking agent etc.

The pH of the composition can be controlled or adjusted by the proper selection of excipients. It should be borne in mind that amlodipine maleate is slightly acidic. For example, amlodipine maleate has a pH of about 4.8 as a saturated aqueous solution. Thus using excipients that are pH inert; i.e., they have little to no effect on pH, generally results in a non-alkaline pharmaceutical composition because the amlodipine maleate essentially acts as its own adjusting agent. An example of a pH-inert excipient is microcrystalline cellulose. A composition comprising amlodipine maleate and microcrystalline cellulose generally exhibits a pH of about 6. Commercially available tablets comprising amlodipine besylate and sold under brand name Norvasc exhibit a pH typically between 7.05–7.35 (again measured as a 20 wt % slurry).

Excipients having a pH effect can also be used. The pH of these excipients must be taken into account in developing the pharmaceutical composition so that the overall pH of the pharmaceutical composition falls within the range of about 5.5 to 7.0.

For example, the commercially available/ pharmaceutically acceptable calcium phosphates are generally alkaline; i.e. pH greater than 7 when measured as described above in a 20% slurry. For instance, DI-TAB, a commercially available dibasic calcium phosphate dihydrate, is reported as having a pH of about 7.4. Nonetheless some forms and grades of calcium phosphate are acidic or neutral pH. This lower pH can be due to the species of calcium phosphate as well as the treatment during processing of the material, such as in removing impurities/washing. For example, dibasic calcium phosphate anhydrate is generally considered to have a pH of about 7.3 whereas A-Tab™ (Rhodia), also a dibasic calcium phosphate anhydrate, has a pH of about 5.0. Further examples of commercially available non-alkaline calcium phosphates include DiCAFOS A (Budenheim) having a pH of about 7 (10% slurry) and Fujicalin SG (Fuji) having a pH from 6.1–7.2 (5% slurry). By using a non-alkaline calcium phosphate as an excipient, a pharmaceutical composition meeting the desired pH can be attained. Alternatively, a blend of calcium phosphates, some at pH above 7 and some a pH below 7 can be used to achieve the desired pH of the composition.

Instead of, or in addition to a non-alkaline calcium phosphate, other acidic excipients can be used by themselves or to counter balance an alkaline excipient. An example of such an acidic excipient is the disintegrant Explotab(™) of Penwest, which is a cross-linked, low substituted sodium starch glycollate. Further, pH adjusting agents can also be used to attained the desired pH. These agents include pharmaceutically acceptable acids such as maleic acid, citric acid or ascorbic acid (the second two have utility also to act as antioxidants) and pharmaceutically acceptable bases such as calcium oxide or magnesium oxide. Salts of weak acids and/or weak bases are also suitable pH adjustors as they act as buffers imparting pH to lower or higher values according to the chemical nature of their components.

The pharmaceutical compositions of the present invention are not particularly limited in terms of form or route of administration. Oral dosage forms as well as parenteral dosage forms are included. The composition can be in the form of a liquid, solid, or suspension. Preferably, the pharmaceutical composition is a solid dosage form such as a tablet, capsule or sachet intended for oral administration.

Preferred solid dosage forms contain as a major excipient microcrystalline cellulose, a calcium phosphate, especially calcium hydrogenphosphate, or a combination thereof. The sum of the other excipients, if any, is generally less than 25 wt %, more usually less than 10 wt % and in some cases less than 5 wt % of the total pharmaceutical composition. Preferred other excipients are a disintegrant such as sodium starch glycollate and/or a lubricant such as magnesium stearate and/or talc.

For example, a pharmaceutical composition comprising amlodipine maleate and microcrystalline cellulose as the only excipient has been shown to provide good stability against the formation of impurities.

The pharmaceutical compositions of the present invention can be made by techniques generally known in the art. In general, the amlodipine maleate is mixed with one or more excipients to form a blend. The mixing can be carried out wet or dry (i.e. using or not using a solvent or a liquid diluent in the process) and can involve granulating, slugging, or blending of powders. A dry process is however preferred. The blend, after optional further processing, can be compressed into tablets or filled into capsules such as gelatin capsules. Typically the amlodipine maleate to be mixed is in the form of particles. The storage stability of the pharmaceutical composition of the present invention is enhanced, in general, by using larger particle sizes. Preferably the average particle size of the amlodipine maleate is at least 20 microns, more preferably at least 100 microns, and in some embodiments at least 300 microns. If an adjustment of the pH of the composition is needed, it preferably is adjusted before processing into the final form such as a tablet or capsule.

For example, tablets made of the present invention can be prepared, e.g. by a wet granulation of a mixture of amlodipine maleate and a solid carrier/diluent such as calcium phosphate of the proper grade, with the aid of a granulating solvent such as water or ethanol; drying the wet granulate; sieving the granulate; blending with sodium starch glycollate and magnesium stearate and compressing the tablet mixture into tablets. The control of pH and/or adjusting the pH value should be advantageously included before blending with magnesium stearate. In this example both the granulating step and the blending step are considered as "mixing" steps since amlodipine maleate and an excipient are mixed.

Yet another suitable process comprises direct compression of the blend of amlodipine maleate and excipient(s). In this process, the ingredients are blended together to form a compressible blend composition that is subsequently compressed into a tablet. A blend that comprises amlodipine maleate, microcrystalline cellulose and/or calcium phosphate, and optionally sodium starch glycollate and/or magnesium stearate may be useful in forming a tablet by direct compression. For example, a blend comprising amlodipine maleate, calcium hydrogen phosphate, microcrystalline cellulose and sodium starch glycollate having a pH of 5.5 to 7.0 can be blended together, re-blended with magnesium stearate and pressurized to form a stable tablet.

The tablets of the present invention comprising amlodipine maleate, microcrystalline cellulose, sodium starch glycollate and magnesium stearate, optionally with addition of calcium hydrogenphosphate, does not suffer from the problem of stickiness to the tablet punch as reported in prior art regarding other amlodipine formulations (see the above cited EP 244 944). Accordingly, the composition of the present invention may be produced in industrial scale without technological problems.

Tablets may be covered with a suitable coating. For example, the coating can be a moisture or light barrier to help with storage stability or a sustained or delayed release coating composition as are well known in the art.

Alternative dosage forms are capsules, both soft and hard capsules. The stabilized amlodipine maleate composition of the invention as described above is filled into capsules by techniques known in the art, in amounts comprising the desired therapeutical dose of amlodipine.

Suitable package material for packing the pharmaceutical dosage forms are plastic or glass containers and blisters. Particularly blisters made from non-permeable materials (high density polyethylene or aluminium) are advantageous as they may contribute to decreasing the rate of formation of degradation impurities, namely the amlo-pyridine impurity, during storage.

The pharmaceutical compositions of the present invention are used in treating or preventing angina or hypertension, as previously defined, by administering an effective amount of the pharmaceutical composition to a patient in need thereof. Typically the pharmaceutical composition is a unit dose. Individual unit dose compositions generally contain from 1 to 100 mg of amlodipine maleate, more usually from 1 to 25 mg. Preferable are unit doses comprising amlodipine maleate in an equivalent of 1.25, 2.5, 5 or 10 mg of amlodipine, such as tablets or capsules for oral administration. The pharmaceutical composition is administered from 1 to 3 times daily, preferably once a day. The above compositions are useful also in reducing of heart failure symptoms, improving systolic left ventricular function and increasing exercise capacity in patients with ischaemic LVD and heart failure without current angina.

Amlodipine maleate compositions of our invention may be also used in medical applications in combination with other antihypertensive and/or antianginal agents, for instance with ACE-inhibitors such as benazepril. The combination may be realized in a form of single combination preparation, e.g. a capsule containing amlodipine maleate and benazepril hydrochloride, or by separate administration of drugs containing the above agents. Similarly, amlodipine maleate may also be combined with HMG-CoA reductase inhibitors such as lovastatin, simvastatin, atorvastatin as well as other statins.

Accordingly, the present invention further provides a method for treating and/or preventing any one or more of angina and hypertension by administering a pharmaceutical composition of our invention comprising an effective and/or prophylactic amount of amlodipine maleate to a sufferer in need thereof.

The present invention also provides the use of the composition of the invention in the manufacture of a medicament for treating and/or preventing any one or more of the Disorders.

EXAMPLES

Example 1

Amlodipine Maleate Tablets Based on Calcium Phosphate Excipient

| a) Tablet compositions comprising calcium phosphate of different pH | | | | | | |
|---|---|---|---|---|---|---|
| Batch number | (A) | (B) | (C) | (D) | (E) | (F) |
| Equivalent of amlodipine | 2.5 mg | 10 mg | 2.5 mg | 10 mg | 2.5 mg | 10 mg |
| Amlodipine maleate | 3.21 mg | 12.8 mg | 3.21 mg | 12.8 mg | 3.21 mg | 12.8 mg |
| Calcium hydrogen phosphate anhydrous: | | | | | | |
| Di CAFOS A | 31.5 mg | 126.0 mg | | | | |
| A-TAB | | | 31.5 mg | 126.0 mg | | |
| Fujicalin | | | | | 31.5 mg | 126.0 mg |
| Microcrystalline cellulose | 62.05 mg | 248.1 mg | 62.05 mg | 248.1 mg | 62.05 mg | 248.1 mg |
| Sodium starch glycollate | 2.0 mg | 8.0 mg | 2.0 mg | 8.0 mg | 2.0 mg | 8.0 mg |
| Magnesium Stearate | 1.0 mg | 4.0 mg | 1.0 mg | 4.0 mg | 1.0 mg | 4.0 mg |
| Total | 99.76 mg | 398.9 mg | 99.76 mg | 398.9 mg | 99.76 mg | 398.9 mg |

| Types of anhydrous calcium hydrogenphosphate used | | | | |
|---|---|---|---|---|
| Batch no. | Final pH of 20% (m/V) slurry of tabs | Type of CaHPO$_4$. | Supplier of CaHPO$_4$. | pH of 5% (m/V) slurry of CaHPO$_4$ | pH of 20% (m/V) slurry of CaHPO$_4$ |
| (A), (B) | 6.13, 6.19 | Di CAFOS A | Budenheim | 7.29 | 6.69 |
| (E), (F) | 5.74, 5.74 | Fujicalin | Fuji | 6.12 | 5.62 |
| (C), (D) | 5.53, 5.54 | A-TAB | Rhone-Poulenc | 6.03 | 5.25 |

| b) Tablet compositions comprising amlodipine maleate of different particle sizes | | | |
|---|---|---|---|
| Batch number | (G) | (H) | (I) |
| Equivalent of amlodipine base | 2.5 mg | 10 mg | 2.5 mg |
| Amlodipine maleate, milled | 3.21 mg | 12.8 mg | — |
| Amlodipine maleate | — | — | 3.21 mg |
| Calciumhydrogen-phosphate anhydrous (pH 6.7) | 31.5 mg | 126.0 mg | 31.5 mg |
| Microcrystalline cellulose | 62.05 mg | 248.1 mg | 62.05 mg |
| Sodium starch glycollate | 2.0 mg | 8.0 mg | 2.0 mg |
| Magnesium Stearate | 1.0 mg | 4.0 mg | 1.0 mg |
| Total | 99.76 mg | 398.9 mg | 99.76 mg |

Particle size of the amlodipine maleate substance used for production of batches A–F was measured by laser diffraction and it was proven that less than 90% of particles is smaller than 204 microns and 50% of particles is smaller than 80 microns.

This amlodipine maleate was milled to a particle size of 10–20 microns and used for producing batches (G) and (H). Alternately, another batch of amlodipine maleate with particle sizes 90% less than 11 microns and 50% less than 6 microns was used for producing batch (I).

c) Manufacturing Procedures

Batches (A)–(F) and (I) have been manufactured as follows:
The amlodipine maleate was sieved through a 500 μm screen.
The other excipients have been sieved through a 850 μm screen.
All excipients except magnesium stearate have been mixed in a free fall mixer for 15 minutes at about 25 rpm. Value of pH was checked at 20% aqueous slurry.
Magnesium stearate was added and the powder blend was mixed for another 5 minutes at about 25 rpm.
2.5 mg and/or 10 mg tablets have been compressed using a Korsch EK0 excenter press.

Batches (G) and (H) have been manufactured as follows:
Amlodipine maleate was milled.
The other excipients have been sieved through a 850 μm screen.
All excipients except magnesium stearate have been mixed in a free fall mixer for 15 minutes at about 25 rpm. Value of pH was checked at 20% aqueous slurry.
Magnesium stearate was added and the powder blend was mixed for another 5 minutes at about 25 rpm.
2.5 mg/10 mg tablets have been compressed on Korsch EK0 excenter press.

Example 2
Tablets Comprising Microcrystalline Cellulose a) Composition

| Batch number | (J) | (K) |
|---|---|---|
| Equivalent of amlodipine base | 2.5 mg | 10 mg |
| Amlodipine maleate | 3.21 mg | 12.8 mg |
| Microcrystalline cellulose | 75.55 mg | 302.1 mg |
| Predried potato starch | 20.0 mg | 80.0 mg |
| Magnesium Stearate | 0.5 mg | 2.0 mg |
| Talc | 0.5 mg | 2.0 mg |
| Total | 99.76 mg | 398.9 mg |

Manufacturing Process

Amlodipine maleate was sieved through a 500 μm screen.
The other excipients have been sieved through a 850 μm screen.
All excipients except magnesium stearate and talc have been mixed in a free fall mixer for 15 minutes at about 25 rpm. Value of pH was checked at 20% aqueous slurry.
Magnesium stearate and talc were added and the powder blend was mixed for another 5 minutes at about 25 rpm.
2.5 mg and 10 mg tablets have been compressed using a Korsch EK0 excenter press.

Properties of Tablet Composition:
pH of 20% (w/V) slurry:—Batch (J)=5.92
Batch (K)=5.96

Example 3
Amlodipine Maleate Tablets Comprising Mannitol

Composition

| Batch number | (L) |
|---|---|
| Equivalent of amlodipine base | 10 mg |
| Amlodipine maleate | 12.8 mg |
| Mannitol | 370.1 mg |
| Sodium starch glycollate | 8.0 mg |
| Magnesium Stearate | 6.0 mg |
| Talc | 2.0 mg |
| Total | 398.9 mg |

Manufacturing Procedure

Amlodipine maleate was sieved through a 500 μm screen.
The other excipients have been sieved through a 850 μm screen.
All excipients except magnesium stearate and talc have been mixed in a free fall mixer for 15 minutes at about 25 rpm. Value of pH was checked at 20% aqueous slurry.
Magnesium stearate and talc were added and the powder blend was mixed for another 5 minutes at about 25 rpm.
10 mg tablets have been compressed using a Korsch EK0 excenter press.

Example 4
Amlodipine Maleate Tablets Having pH Higher than 7 (Comparative Example)

Composition (pH of the 20% w/v slurry: 8.68)

| Batch number | (X) |
|---|---|
| Equivalent of amlodipine base | 2.5 mg |
| Amlodipine maleate | 3.21 mg |
| Calcium hydrogenphosphate anhydrous (pH 6.69) | 31.5 mg |
| Magnesium oxide ponderosum | 0.5 mg |
| Microcrystalline cellulose | 62.05 mg |
| Sodium starch glycollate | 2.0 mg |
| Magnesium Stearate | 1.0 mg |
| Total | 100.26 mg |

Manufacturing Process

The amlodipine maleate was sieved through a 500 μm screen.
The other excipients have been sieved through a 850 μm screen.
Amlodipine maleate, magnesium oxide and about 30% of the amount of microcrystalline cellulose (MCC) were mixed in a free fall mixer for 10 minutes at about 25 rpm.
The remaining amount of MCC, calcium hydrogenphopsphate anhydrous and sodium starch glycollate were added and the blend was mixed in a free fall mixer for 15 minutes at about 25 rpm. Value of pH was checked at 20% aqueous slurry.
Magnesium stearate was added and the powder blend was mixed for another 5 minutes at about 25 rpm.
2.5 mg tablets and proportionately larger 10 mg tablets have been compressed using a Korsch EK0 excenter press.

Example 5
Stability Studies on Amlodipine Maleate Tablets

Stability studies on batches produced in Examples 1–4 were performed in a thermostated chamber adjusted to 40±2° C. and 75±5% of releative humidity in various package materials (HDPE bottles, PVC/PVDC/PE blisters) or on an open dish. Assay of the active substance and of the content of impurities was performed by HPLC method, using reference materials of amlodipine maleate and major degradation impurities:

amlodipine aspartate (Z#204)

amlo-pyridine (Z# 202)

Apart, two minor impurities Z#203 and Z#205 were detected and identified.

The content of other detected impurities/degradation products was calculated by internal normalization.

In the following tables, the assay of the active substance is expressed in miligrams, the content of impurities is expressed in percent.

A) Stability studies performed at 40° C./75% RH, open dish (influence of pH)

|  | (A) | (B) | (E) | (F) | (C) | (D) |
|---|---|---|---|---|---|---|
| t = 0 months | | | | | | |
| Assay (mg/tab) | 2.45 | 9.85 | 2.38 | 10.01 | 2.38 | 9.88 |
| Z#202 (%) | 0.15 | 0.15 | 0.08 | 0.08 | 0.05 | 0.08 |
| Z#203 (%) | 0.00 | 0.03 | 0.03 | 0.03 | 0.03 | 0.03 |
| Z#204 (%) | 0.16 | 0.15 | 0.13 | 0.12 | 0.13 | 0.12 |
| Z#205 (%) | 0.01 | 0.01 | 0.00 | 0.00 | 0.00 | 0.00 |
| Tot. unknown (%) | 0.31 | 0.28 | 0.27 | 0.28 | 0.27 | 0.27 |
| T = 1 month | | | | | | |
| Assay (mg/tab) | 2.48 | 9.82 | 2.31 | 9.55 | 2.23 | 9.29 |
| Z#202 (%) | 0.15 | 0.15 | 0.21 | 0.23 | 1.27 | 1.25 |
| Z#203 (%) | 0.00 | 0.03 | 0.04 | 0.04 | 0.04 | 0.04 |
| Z#204 (%) | 0.24 | 0.23 | 0.41 | 0.30 | 0.27 | 0.22 |
| Z#205 (%) | 0.01 | 0.01 | 0.03 | 0.02 | 0.04 | 0.03 |
| Tot. unknown (%) | 0.35 | 0.31 | 0.58 | 0.56 | 0.83 | 0.72 |
| T = 3 months | | | | | | |
| Assay (mg/tab) | 2.40 | 9.69 | 2.30 | 9.57 | 2.16 | 8.94 |
| Z#202 (%) | 0.20 | 0.18 | 0.37 | 0.39 | 1.85 | 1.85 |
| Z#203 (%) | 0.03 | 0.03 | 0.04 | 0.05 | 0.04 | 0.04 |
| Z#204 (%) | 0.31 | 0.29 | 0.77 | 0.63 | 0.33 | 0.27 |
| Z#205 (%) | 0.01 | 0.01 | 0.05 | 0.04 | 0.03 | 0.02 |
| Tot. unkn. (%) | 0.42 | 0.35 | 1.11 | 1.10 | 1.37 | 1.10 |

Stability studies performed in PVC/PE/PVDC blister at 40° C./75% RH

|  | (A) | (B) | (J) | (K) |
|---|---|---|---|---|
| T = 0 months | | | | |
| Assay | 2.51 | 9.99 | 2.52 | 10.33 |
| Z#202 | 0.11 | 0.11 | 0.20 | 0.20 |
| Z#203 | 0.00 | 0.00 | 0.00 | 0.00 |
| Z#204 | 0.15 | 0.14 | 0.00 | 0.00 |
| Z#205 | 0.01 | 0.01 | 0.00 | 0.00 |
| t unkn. | 0.31 | 0.31 | 0.46 | 0.49 |
| T = 3 months | | | | |
| Assay | 2.49 | 9.49 | 2.49 | 9.99 |
| Z#202 | 0.15 | 0.15 | 0.07 | 0.05 |
| Z#203 | 0.00 | 0.00 | 0.00 | 0.03 |
| Z#204 | 0.26 | 0.29 | 0.46 | 0.40 |
| Z#205 | 0.01 | 0.01 | 0.02 | 0.02 |
| t unkn. | 0.36 | 0.34 | 0.45 | 0.38 |
| T = 6 months | | | | |
| Assay | 2.45 | 9.49 | 2.45 | 9.94 |
| Z#202 | 0.23 | 0.21 | 0.17 | 0.11 |
| Z#203 | 0.04 | 0.04 | 0.04 | 0.04 |
| Z#204 | 0.46 | 0.39 | 0.64 | 0.54 |
| Z#205 | 0.01 | 0.00 | 0.02 | 0.02 |
| t unkn. | 0.57 | 0.54 | 0.64 | 0.51 |

Stability studies performed open dish at 40° C./75% RH

|  | (J) | (K) |
|---|---|---|
| t = 0 months | | |
| Assay | 2.49 | 10.18 |
| Z#202 | 0.04 | 0.04 |
| Z#203 | 0.02 | 0.03 |
| Z#204 | 0.19 | 0.17 |
| Z#205 | 0.01 | 0.01 |
| tot unkn. | 0.42 | 0.36 |
| t = 1 month | | |
| Assay | 2.44 | 10.14 |
| Z#202 | 0.08 | 0.07 |
| Z#203 | 0.02 | 0.03 |
| Z#204 | 0.34 | 0.36 |
| Z#205 | 0.01 | 0.01 |
| tot unkn. | 0.45 | 0.42 |
| t = 3 months | | |
| assay | 2.41 | 9.72 |
| Z#202 | 0.22 | 0.21 |

-continued

Stability studies performed open dish at 40° C./75% RH

|  | (J) | (K) |
|---|---|---|
| Z#203 | 0.04 | 0.04 |
| Z#204 | 0.50 | 0.54 |
| Z#205 | 0.03 | 0.03 |
| tot unkn. | 0.63 | 0.56 |

Stability studies performed in HDPE container at 40° C./75% RH

|  | (A) | (B) | (J) | (K) | (L) |
|---|---|---|---|---|---|
| T = 0 months | | | | | |
| Assay | 2.51 | 9.99 | 2.52 | 10.33 | 10.11 |
| Z#202 | 0.11 | 0.11 | 0.20* | 0.20* | 0.19* |
| Z#203 | 0.00 | 0.00 | 0.00 | 0.00 | 0.00 |
| Z#204 | 0.15 | 0.14 | 0.00* | 0.00* | 0.00* |
| Z#205 | 0.01 | 0.01 | 0.00 | 0.00 | 0.00 |
| t unkn. | 0.31 | 0.31 | 0.46 | 0.49 | 0.40 |
| T = 3 month | | | | | |
| Assay | 2.52 | 9.84 | 2.51 | 10.26 | 8.69 |
| Z#202 | 0.13 | 0.15 | 0.41* | 0.37* | 0.45* |
| Z#203 | 0.00 | 0.00 | 0.03 | 0.00 | 0.05 |
| Z#204 | 0.27 | 0.23 | 0.00* | 0.00* | 0.00* |
| Z#205 | 0.03 | 0.03 | 0.07 | 0.05 | 0.01 |
| t unkn. | 0.33 | 0.32 | 0.41 | 0.49 | 0.66 |
| T = 6 months | | | | | |
| Assay | 2.49 | 9.83 | 2.47 | 10.26 | |
| Z#202 | 0.15 | 0.15 | 0.08 | 0.05 | |
| Z#203 | 0.00 | 0.00 | 0.00 | 0.03 | |
| Z#204 | 0.44 | 0.41 | 0.44 | 0.38 | |
| Z#205 | 0.02 | 0.01 | 0.10 | 0.08 | |
| t unkn. | 0.46 | 0.44 | 0.44 | 0.37 | |

*Values for Z#202 and Z#204 together

Comparative stability studies performed at the composition with alkaline pH (open dish, 40° C./75% RH

|  | (X) |
|---|---|
| t = 0 months | |
| Assay | 2.52 |
| Z#202 | 0.04 |
| Z#203 | 0.03 |
| Z#204 | 0.13 |
| Z#205 | 0.00 |
| tot unkn. | 0.30 |
| t = 1 month | |
| Assay | 2.43 |
| Z#202 | 0.06 |
| Z#203 | 0.03 |
| Z#204 | 1.73 |
| Z#205 | 0.00 |
| tot unkn. | 0.51 |

Stability studies performed at 40° C./75% RH, open dish (influence of particle size)

|  | (A) | (B) | (G) | (H) | (I) |
|---|---|---|---|---|---|
| t = 0 months | | | | | |
| Assay (mg/tab) | 2.45 | 9.85 | 2.38 | 10.12 | 2.54 |
| Z#202 (%) | 0.15 | 0.15 | 0.05 | 0.05 | 0.10 |
| Z#203 (%) | 0.00 | 0.03 | 0.00 | 0.01 | 0.04 |
| Z#204 (%) | 0.16 | 0.15 | 0.03 | 0.03 | 0.01 |
| Z#205 (%) | 0.01 | 0.01 | 0.00 | 0.00 | 0.02 |
| Tot unkn. (%) | 0.31 | 0.28 | 0.17 | 0.11 | 0.26 |
| t = 1 month | | | | | |
| Assay (mg/tab) | 2.48 | 9.82 | 2.29 | 9.88 | — |
| Z#202 (%) | 0.15 | 0.15 | 0.17 | 0.14 | — |
| Z#203 (%) | 0.00 | 0.03 | 0.01 | 0.01 | — |
| Z#204 (%) | 0.24 | 0.23 | 0.52 | 0.48 | — |
| Z#205 (%) | 0.01 | 0.01 | 0.02 | 0.02 | — |
| Tot unkn. (%) | 0.35 | 0.31 | 0.22 | 0.19 | — |
| t = 2 months | | | | | |
| Assay (mg/tab) | 2.46 | 9.87 | 2.22 | 9.64 | 2.35 |
| Z#202 (%) | 0.17 | 0.16 | 0.28 | 0.25 | 0.34 |
| Z#203 (%) | 0.00 | 0.00 | 0.01 | 0.01 | 0.03 |
| Z#204 (%) | 0.28 | 0.28 | 1.02 | 1.01 | 0.41 |
| Z#205 (%) | 0.01 | 0.01 | 0.03 | 0.03 | 0.04 |
| Tot unkn. (%) | 0.47 | 0.43 | 0.63 | 0.52 | 0.60 |
| t = 3 months | | | | | |
| Assay (mg/tab) | 2.40 | 9.69 | 2.24 | 9.36 | 2.36 |
| Z#202 (%) | 0.20 | 0.18 | 0.18 | 0.16 | 0.39 |
| Z#203 (%) | 0.03 | 0.03 | 0.01 | 0.01 | 0.11 |
| Z#204 (%) | 0.31 | 0.29 | 1.26 | 1.34 | 0.53 |
| Z#205 (%) | 0.01 | 0.01 | 0.05 | 0.04 | 0.04 |
| Tot unkn. (%) | 0.42 | 0.35 | 0.90 | 0.74 | 0.64 |

For a comparison of stability, increase in total impurities, identified and unidentified, with regard to the t = 0 months level, is considered:

| increase in total impurities in % | (A) | (B) | (G) | (H) | (I) |
|---|---|---|---|---|---|
| after 3 months at 40° C./75% RH | +0.33 | +0.24 | +1.82 | +1.43 | +1.28 |

Comparative Stability Study with Norvasc (Commercial Amlodipine Besylate Tablets)

Stability Studies Performed in Original Blister at 40° C./75% RH

|  | Norvasc ® 5 mg batch 81040100 (DE) | Norvase ® 10 mg batch 901-05941 (NL) |
|---|---|---|
| t = 0 months | | |
| Assay | 5.19 | 9.99 |
| Z#202 | 0.04 | 0.02 |
| Z#203 | 0.01 | 0.00 |
| Z#204 | 0.00 | 0.00 |
| Z#205 | 0.00 | 0.00 |
| tot. unkn. | 0.12 | 0.12 |
| t = 3 months | | |
| Assay | 5.13 | 9.70 |
| Z#202 | 0.16 | 0.17 |
| Z#203 | 0.03 | 0.00 |
| Z#204 | 0.00 | 0.00 |

-continued

|  | Norvasc ® 5 mg batch 81040100 (DE) | Norvasc ® 10 mg batch 901-05941 (NL) |
|---|---|---|
| Z#205 | 0.00 | 0.00 |
| tot. unkn. | 0.38 | 0.62 |
| t = 6 months | | |
| Assay | 4.97 | 9.58 |
| Z#202 | 0.28 | 0.27 |
| Z#203 | 0.00 | 0.00 |
| Z#204 | 0.00 | 0.00 |
| Z#205 | 0.00 | 0.00 |
| tot. unkn. | 0.49 | 0.78 |

Stability studies performed on open dish at 40° C./75% RH

|  | Norvasc ® 2.5 mg batch 8QP115A (US) | Norvasc ® 10 mg batch N-09 (ES) |
|---|---|---|
| t = 0 months | | |
| Assay | 2.44 | 9.91 |
| Z#202 | 0.08 | 0.82 |
| Z#203 | 0.00 | 0.00 |
| Z#204 | 0.00 | 0.00 |
| Z#205 | 0.00 | 0.00 |
| tot. unkn. | 0.02 | 0.34 |
| t = 1 months | | |
| Assay | 2.44 | 8.90 |
| Z#202 | 0.18 | 2.17 |
| Z#203 | 0.04 | 0.19 |
| Z#204 | 0.00 | 0.01 |
| Z#205 | 0.00 | 0.00 |
| tot. unkn. | 0.10 | 1.21 |
| t = 2 months | | |
| Assay | 2.39 | 7.98 |
| Z#202 | 0.27 | 3.24 |
| Z#203 | 0.00 | 0.00 |
| Z#204 | 0.00 | 0.00 |
| Z#205 | 0.00 | 0.03 |
| tot. unkn. | 0.33 | 2.51 |
| t = 3 months | | |
| Assay | 2.34 | 7.68 |
| Z#202 | 0.37 | 3.98 |
| Z#203 | 0.00 | 0.00 |
| Z#204 | 0.00 | 0.00 |
| Z#205 | 0.00 | 0.03 |
| tot. unkn. | 0.27 | 2.76 |

Example 6

Amlodipine Maleate Capsules

Compositions

| Batch number | (CA), (CB) |
|---|---|
| Equivalent to amlodipine | 5.0 mg |
| Amlodipine maleate | 6.42 mg |
| Microcrystalline cellulose | 72.6 mg |
| Predried potato starch | 20.0 mg |
| Magnesium stearate | 0.5 mg |
| Total | 99.52 mg |

| Batch number | CC | CX |
|---|---|---|
| Equivalent to amlodipine | 5.0 mg | 5.0 mg |
| Amlodipine maleate | 6.42 mg | 6.42 mg |
| Calcium hydrogenphosphate anhydrous | 31.5 mg | 31.5 mg |
| Magnesium oxide | — | 1.5 mg |
| Microcrystalline cellulose | 62.0 mg | 62.0 mg |
| Sodium starch glycollate | 2.0 mg | 2.0 mg |
| Magnesium stearate | 1.0 mg | 1.0 mg |
| Total | 102.92 mg | 104.43 mg | pH at capsules at t = 0

| Batch no. | Strength | Type of Calcium hydrogenphosphate anhydrous | pH of 20% (m/V) slurry of capsule content |
|---|---|---|---|
| (CC) | 5.0 mg | Di CAFOS A | 6.10 |
| (CX) | 5.0 mg | Di CAFOS A | 9.59 |

Batch (CA) has been manufactured as follows:
The amlodipine maleate was sieved through a 500 µm screen.
The other excipients have been sieved through a 850 µm screen.
All excipients except magnesium stearate have been mixed in a free fall mixer for 15 minutes at about 25 rpm. pH value was checked in 20% aqueous slurry.
Magnesium stearate was added and the powder blend was mixed for another 5 minutes at about 25 rpm.
gelatine capsules have been filled with this powder blend Batch (CB) Has Been Manufactured as Follows:
The amlodipine maleate was sieved through a 500 µm screen.
The other excipients have been sieved through a 850 µm screen.
All excipients except magnesium stearate have been mixed in a free fall mixer for 15 minutes at about 25 rpm. pH value was checked in 20% aqueous slurry.
Magnesium stearate was added and the powder blend was mixed for another 5 minutes at about 25 rpm.
HPMC capsules have been filled with this powder blend.

Batch (CC) Has Been Manufactured as Follows:
The amlodipine maleate was sieved through a 500 µm screen.
The other excipients have been sieved through a 850 µm screen.
All excipients except magnesium stearate have been mixed in a free fall mixer for 15 minutes at about 25 rpm. pH value was checked in 20% aqueous slurry.
Magnesium stearate was added and the powder blend was mixed for another 5 minutes at about 25 rpm.
gelatine capsules have been filled with this powder blend.

Batch (CX) Has Been Manufactured as Follows:
The amlodipine maleate was sieved through a 500 µm screen.
The other excipients have been sieved through a 850 µm screen.
Amlodipine maleate, magnesium oxide and about 30% of the amount of microcrystalline cellulose (MCC) were mixed in a free fall mixer for 10 minutes at about 25 rpm.
The remaining amount of MCC, calcium hydrogenphosphate anhydrous and sodium starch glycollate were added and the blend was mixed in a free fall mixer for 15 minutes at about 25 rpm. pH value was checked in 20% aqueous slurry.

Magnesium stearate was added and the powderblend was mixed for another 5 minutes at about 25 rpm.

gelatine capsules have been filled with this powderblend, using an automatic capsule filling machine.

Example 7

Stability Studies on Amlodipine Maleate Capsules

Stability studies on batches prepared in Example 6 were performed essentially as described in Example 5.

| Stability studies performed in PVC/PE/PVDC blister at 40° C./75% RH | | |
|---|---|---|
| | (CA) | (CB) |
| t = 0 months | | |
| Assay | 5.13 | 4.98 |
| Z#202 | 0.04 | 0.04 |
| Z#203 | 0.03 | 0.03 |
| Z#204 | 0.12 | 0.12 |
| Z#205 | 0.00 | 0.00 |
| tot unkn. | 0.32 | 0.31 |
| t = 3 months | | |
| Assay | 4.82 | 4.76 |
| Z#202 | 0.08 | 0.06 |
| Z#203 | 0.02 | 0.02 |
| Z#204 | 0.15 | 0.14 |
| Z#205 | 0.01 | 0.00 |
| tot unkn. | 0.39 | 0.38 |
| t = 6 months | | |
| Assay | 4.67 | 4.81 |
| Z#202 | 0.14 | 0.10 |
| Z#203 | 0.04 | 0.02 |
| Z#204 | 0.23 | 0.18 |
| Z#205 | 0.02 | 0.01 |
| tot unkn. | 0.45 | 0.42 |

| Two one month stability studies performed in open dish | | |
|---|---|---|
| | (CC) | (CX) |
| t = 0 months | | |
| Assay | 4.91 | 4.72 |
| Z#202 | 0.04 | 0.04 |
| Z#203 | 0.03 | 0.04 |
| Z#204 | 0.12 | 0.13 |
| Z#205 | 0.00 | 0.00 |
| tot unkn. | 0.28 | 0.29 |
| T = 1 month @ 25° C./60% RH | | |
| Assay | 4.85 | 4.70 |
| Z#202 | 0.05 | 0.05 |
| Z#203 | 0.04 | 0.04 |
| Z#204 | 0.13 | 0.14 |
| Z#205 | 0.00 | 0.00 |
| tot unkn. | 0.28 | 0.28 |
| T = 1 month @ 40° C./75% RH | | |
| Assay | 4.76 | 4.16 |
| Z#202 | 0.06 | 0.08 |
| Z#203 | 0.04 | 0.03 |
| Z#204 | 0.15 | 11.36 |
| Z#205 | 0.00 | 0.00 |
| tot unkn. | 0.28 | 0.62 |

| Stability studies performed in HDPE container | | |
|---|---|---|
| | (CA) | (CB) |
| t = 0 months | | |
| Assay | 4.99 | 5.01 |
| Z#202 | 0.05 | 0.04 |
| Z#203 | 0.03 | 0.03 |
| Z#204 | 0.12 | 0.11 |
| Z#205 | 0.00 | 0.00 |
| tot unkn. | 0.31 | 0.30 |
| T = 3 months @ 25° C./60% RH | | |
| Assay | 5.07 | 4.77 |
| Z#202 | 0.04 | 0.04 |
| Z#203 | 0.03 | 0.04 |
| Z#204 | 0.12 | 0.12 |
| Z#205 | 0.00 | 0.00 |
| tot unkn. | 0.30 | 0.32 |
| T = 3 months @ 40° C./75% RH | | |
| Assay | 5.01 | 4.65 |
| Z#202 | 0.05 | 0.05 |
| Z#203 | 0.03 | 0.04 |
| Z#204 | 0.12 | 0.13 |
| Z#205 | 0.00 | 0.00 |
| tot unkn. | 0.29 | 0.32 |

Stability Studies on Commercially Available Amlor® (Amlodipine Besylate) Capsules

| Stability studies performed in original blister | | |
|---|---|---|
| Amlor 5 mg capsules batch 9037002 | t = 0 months | t = 3 months 40° C./75% RH |
| Assay | 4.59 | 4.44 |
| Z#202 | 0.01 | 0.20 |
| Z#203 | 0.00 | 0.00 |
| Z#204 | 0.00 | 0.00 |
| Z#205 | 0.00 | 0.00 |
| tot unkn. | 0.06 | 0.37 |

The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. A pharmaceutical composition comprising an effective amount of amlodipine maleate and at least one pharmaceutically acceptable excipient wherein said composition has a pH within the range of 5.5–6.8 and is in solid form.

2. The composition according to claim 1, wherein said composition has a pH of about 6.0–6.8.

3. The composition according to claim 1, wherein said excipient is calcium phosphate or microcrystalline cellulose.

4. The composition according to claim 3, wherein said composition comprises calcium phosphate and microcrystalline cellulose.

5. The composition according to claim 3, wherein said excipient is calcium hydrogen phosphate.

6. The composition according to claim 4, wherein said excipient is microcrystalline cellulose.

7. The composition according to claim 1, wherein said composition further comprises an acidic pH adjusting agent.

8. The composition according to claim 1, wherein said composition is in the form of a tablet.

9. The composition according to claim 8, which further comprises an outer layer surrounding said tablet.

10. The composition according to claim 1, wherein said composition is in the form of a capsule.

11. The composition according to claim 1, wherein said amount of amlodipine maleate corresponds to 1.0 to 25 mg of amlodipine free base.

12. The composition according to claim 11, wherein said amount of amlodipine maleate corresponds to 1.25, 2.5, 5 or 10 mg of amlodipine free base.

13. A method for treating angina, hypertension, or heart failure, which comprises administering to a patient in need thereof an effective amount of the composition according to claim 1.

14. A process for making the composition according to claim 1, which comprises mixing amlodipine maleate and at least one pharmaceutically acceptable excipient to form a mixture having a pH within the range of 5.5 to 6.8.

15. A process of making a solid dosage form amlodipine maleate, which comprises mixing amlodipine maleate and at least one pharmaceutically acceptable excipient to form a mixture having a pH of 5.5–6.8.

16. The process according to claim 15, which further comprises compressing said mixture into a tablet.

17. The process according to claim 15, which further comprises filling capsules with said mixture to form a pharmaceutical dosage form.

18. The process according to claim 15, wherein said mixing is carried out by wet granulation.

19. The process according to claim 15, wherein said mixing is carried out by a dry method.

20. The process according to claim 19, wherein said amlodipine maleate is mixed as solid particles having an average particle size of at least 100 microns with said excipient.

21. A tablet made according to the process of claim 15.

22. The composition according to claim 7, wherein said pH adjusting agent is a pharmaceutically acceptable acid.

23. The composition according to claim 22, wherein said pharmaceutically acceptable acid is maleic acid, citric acid, or ascorbic acid.

24. The composition according to claim 23, wherein said pharmaceutically acceptable acid is maleic acid.

25. The composition according to claim 1, wherein said composition comprises an acidic excipient.

26. The composition according to claim 1, wherein said amlodipine maleate has an average particle size of at least 20 microns.

27. The composition according to claim 26, wherein said amlodipine maleate has an average particle size of at least 100 microns.

28. The composition according to claim 1, wherein said composition has a pH within the range of about 5.5–6.2.

29. The composition according to claim 1, wherein said composition has a pH within the range of about 6.0–6.2.

30. The composition according to claim 8, wherein said composition has a pH within the range of about 5.5–6.2.

31. The composition according to claim 1, wherein said excipient is pH inert.

32. The composition according to claim 31, wherein said excipient is microcrystalline cellulose.

33. The composition according to claim 1, wherein at least one excipient is an acidic excipient.

34. The composition according to claim 33, wherein said acidic excipient is a sodium starch glycolate.

35. The composition according to claim 34, which further comprises microcrystalline cellulose.

36. The composition according to claim 35, wherein the sum of excipients other than said microcrystalline cellulose is less than 10 wt % based on the total weight of the composition.

37. The composition according to claim 34, which further comprises a calcium phosphate.

38. The composition according to claim 37, wherein the sum of excipients other than said calcium phosphate is less than 10 wt % based on the total weight of the composition.

* * * * *